(12) United States Patent
Besemer et al.

(10) Patent No.: US 7,947,292 B2
(45) Date of Patent: May 24, 2011

(54) BACTERIA TRAPPING FIBROUS MATERIAL

(75) Inventors: Arie Besemer, Amerongen (NL); Dorine Lisa Van Brussel-Verraest, Bodegraven (NL); Anne-Mieke Verwilligen, Zeist (NL); Gunilla Himmelmann, Molnlycke (SE); Kent Malmgren, Sundsvall (SE); Bo Andreasson, Sundsvall (SE); Carolyn Berland, Molndal (SE)

(73) Assignee: SCA Hygiene Products AB, Gothenburg (SE)

( * ) Notice: Subject to any disclaimer, the term of this patent is extended or adjusted under 35 U.S.C. 154(b) by 768 days.

(21) Appl. No.: 11/987,933

(22) Filed: Dec. 6, 2007

(65) Prior Publication Data

US 2010/0278690 A1    Nov. 4, 2010

Related U.S. Application Data

(62) Division of application No. 10/757,424, filed on Jan. 15, 2004, now abandoned.

(60) Provisional application No. 60/440,028, filed on Jan. 15, 2003.

(51) Int. Cl.
*A01N 25/24* (2006.01)
*A01N 25/34* (2006.01)
*A61K 9/00* (2006.01)
*A61K 9/70* (2006.01)

(52) U.S. Cl. ........ 424/400; 424/402; 424/404; 424/407; 424/443

(58) Field of Classification Search .................. None
See application file for complete search history.

(56) References Cited

U.S. PATENT DOCUMENTS

| 4,026,291 | A | * | 5/1977 | Nagano et al. ............... 604/368 |
| 4,259,958 | A | | 4/1981 | Goodbar |
| 4,708,870 | A | | 11/1987 | Pardini |
| 4,818,598 | A | | 4/1989 | Wong |
| 4,907,579 | A | * | 3/1990 | Kum .............................. 602/58 |
| 6,039,940 | A | * | 3/2000 | Perrault et al. ............ 424/78.06 |
| 2002/0098317 | A1 | | 7/2002 | Jaschinski et al. |
| 2002/0177828 | A1 | | 11/2002 | Batich et al. |

FOREIGN PATENT DOCUMENTS

| AU | BA 25 431/77 | 11/1978 |
| EP | 0 794 223 | 9/1997 |
| EP | 1 291 460 | 3/2003 |
| WO | WO 01/24840 | 4/2001 |
| WO | WO 01/34656 | 5/2001 |
| WO | WO 03/006739 | 1/2003 |

* cited by examiner

*Primary Examiner* — Mark Navarro
(74) *Attorney, Agent, or Firm* — Young & Thompson

(57) ABSTRACT

The invention concerns the use of a fiber modified with functions capable of interacting with microbial cell wall proteins for immobilizing micro-organisms in hygiene products. Those functions are particularly capable of interacting with anionic groups and amine groups, and are especially cationic groups and aldehydes, respectively. The fibers may be synthetic or cellulosic. Also hygiene products containing these fibers are described.

20 Claims, No Drawings

BACTERIA TRAPPING FIBROUS MATERIAL

BACKGROUND OF THE INVENTION

The present invention relates to disposable fibrous materials for immobilising microbes for the purpose of removing or inactivating the microbes, and to a process for producing such fibrous material. The invention furthermore relates to cleaning products and hygiene products containing these fibrous materials for the purpose of removing or controlling microorganisms.

DESCRIPTION OF THE RELATED ART

Bacterial contamination in hygiene products is commonly controlled by incorporating antibacterial agents. Similarly, antibacterial action of cleaning material can be enhanced by incorporation of bactericides. WO 00/58092 (U.S. Pat. No. 6,258,455) discloses an antimicrobial cleaning cloth comprising a cationic polyamide microfibre and an antibacterial cellulose acetate fibre containing an antimicrobial agent, spun together with a polyester fibre for increasing strength. The cloth can be used for scraping bacteria from a surface. In contrast, EP 1247534 describes the use of non-pretreated, dry paper or nonwoven for wiping bacteria from the hands.

U.S. Pat. No. 4,791,063 describes a fibrous separation device for trapping bacteria, wherein the fibre is a cellulose to which a cationic polymer is covalently attached. The cationic polymer can be a poly(meth)acrylate having diethylaminoethyl (DEAE) acrylate units as cationic groups and glycidyl acrylate units as cellulose-binding groups. The DEAE groups may be quaternised. These cellulose derivatives are described as having improved protein absorbing capacity. The cationic polymer can also be a polyionene coupled to cellulose with a crosslinker such as butanediol diglycidyl ether. The resulting cationic cellulose is used as a column material for filtering bacteria from a solution.

Cationic cellulosic fibre is a known product. U.S. Pat. No. 4,505,775 discloses a cationic cellulose obtained by reaction of cellulose fibre with a condensate of epichlorohydrin and dimethylamine. The cationic fibre has improved dye retention characteristics. A more recent survey of cationic cellulose fibres is given in Gruber et al. in *Cellulose Derivatives, Modification, Characterisation and Nanostructures*, Ed. T. J. Heinze and W. G. Glasser, A. C. S., Washington D.C., 1998.

WO 01/92632 (EP 1291460) describes the coupling of basic amino acids such as lysine and arginine to cellulose fibres resulting in low degrees of functionalisation (1.7 and 1.8 substituent group, respectively, per 100 recurring units of the cellulose). The treated fibres are for use as an antibacterial product. US application 2002/0177828 (WO 03/039602) describes wound dressings having a coating grafted with cationised polymethacrylate. The products have antimicrobial properties.

Aldehyde-functionalised cellulosic and other fibres are also known, e.g. from WO99/23117, WO00/50462, WO00/50463 and WO01/34656. They have e.g. improved wet strength when used as a paper or tissue material. Small molecules containing carbonyl groups such as linear (C6-C12) aldehydes, formaldehyde, glyoxal, glutar-aldehyde, acetone, diethyl ketone etc. are known for use as microbiocide or preservative (e.g. EP 0018504, WO01/39739, U.S. Pat. No. 5,807,587).

SUMMARY OF THE INVENTION

It was found that bacteria, moulds and other micro-organisms can be effectively controlled in hygiene products by immobilising them onto fibrous materials of the hygiene products without necessarily killing them. The immobilisation can be effected according to the invention by modifying the fibres with functional groups capable of interacting with the bacterial cell walls. Such functional groups include cationic groups and carbonyl groups, which can be introduced into the fibres by direct chemical modification of the fibrous material. The fibrous material can be part of cleaning cloths, napkins, personal hygiene products and the like. No bactericidal additives are necessary or even desired.

DETAILED DESCRIPTION OF THE INVENTION

The invention pertains to hygiene products containing fibrous materials carrying functional groups capable of interacting with the bacterial cell walls. The hygiene articles can be products for absorbing body fluids which have the risk of bacterial growth. Examples include sanitary napkins and the like having a layer of modified fibre capable of immobilising microorganisms, and thus inhibiting their growth, and sanitary napkins and the like having modified fibres. Another type of products are tissues and other cloth-like articles suitable for cleaning surfaces and containing or consisting of modified fibre.

Functional groups capable of interacting with bacterial cell walls are understood to be functional groups capable of reacting with polar groups on the cell walls, especially on cell-wall proteins. Such groups include carboxyl groups, amino groups, hydroxyl groups and the like, especially (anionic) carboxyl groups and phosphoryl groups such as present in proteins (e.g. glutamic acid, aspartic acid residues), glycoproteins, and certain polysaccharides, and amino (guanidino etc.) groups such as present in proteins (e.g. lysine, arginine residues). The (anionic) carboxyl and phosphoryl groups exhibit electrostatic interaction with cationic groups present on the modified fibres, while amino groups can interact with e.g. aldehyde groups in the modified fibres of the invention.

The fibres containing the functional groups capable of interacting with bacterial cell walls can also be denoted as electrophilically modified, which refers to chemical modification resulting in the presence of electrophilic functional groups. The electrophilic groups can be the electropositively charged groups, i.e. cationic groups, wherein the positive charge has the electrophilic function, or they can be non-charged groups that have an internal charge separation wherein the positively charged centre is capable of reacting with electron-rich functions.

Examples of electropositive groups include common cationic groups such as ammonium groups, phosphonium groups, sulphonium groups and certain metal-containing groups. Examples of non-charged groups with internal charge separation include carbonyl groups, such as aldehydes, ketones, and the like. For example, the internal charge separation in an aldehyde can be represented by the variant form R—HC$^+$—O$^-$ of the conventional neutral formula R—HC=O. The partially charged carbon atom is capable of reacting with nucleophiles such as hydroxyl groups and amino groups.

Although the inventors do not wish to be bound by theory, a possible explanation of the bacteria-trapping property of the modified fibres is their capability of associating with outer layers of the bacteria having electron-rich functions, such as carboxyl groups, amino groups and the like. Thus, a common feature of the cationic functions and the non-charged electrophilic functions may well be their capability to associate carboxyl groups or the like. Herebelow, the functional (electrophilic) groups of the modified fibres of the invention are further illustrated as cationic groups and aldehyde groups, but other functional (electrophilic) groups capable of interacting with cell wall biopolymers can be used similarly.

The functional groups may be the same throughout the modified fibre. Also, the same fibres may contain different functional groups such as cationic groups and carbonyl groups in the same molecule, but they may also be a fibre containing different molecules, e.g. one type containing cationic groups, another containing carbonyl groups. Also the fibre may partly consist of modified fibres containing the functional groups capable of interacting with protein functions, and partly of non-modified fibre, or fibre containing functional groups having less or no interaction with cell wall bio-polymer functions, such as hydroxyalkyl or acyl groups.

The invention more particularly relates to layered products, in which at least one layer, preferably a surface layer, contains modified fibre. Thus, the product can be an absorbing or wiping sheet having different layers, wherein at least one layer contains the modified fibre, and at least one layer preferably does not contain the modified fibre. If the layers are designated as E for (electrophilically) modified fibre layer and N for non-modified fibre layer, the layered structure can be of the types E-N, E-N-E, E-N-N, E-E-N, N-E-N, E-N-N-N, E-N-N-E and the like, wherein those structures having an external modified fibre layer (E) are preferred.

The product of the invention can also be a homogeneous product containing a mixture of modified fibres and non-modified fibres. The basic fibres can than be the same, e.g. cellulosic, or they can be different, e.g. a non-modified synthetic fibre combined with a modified cellulosic fibre or vice versa. Also, the product can be layered, wherein one or more layers may consist of a mixture of modified and non-modified fibres as described above.

The product of the invention can also be a multiple sheet product, i.e. a layered structure consisting of distinct superposed sheets, each sheet containing one or more layers. In such multiple sheet products, one top sheet can entirely consist of electrophilically modified fibre, or may only contain an electrophilically modified surface layer together with one or more non-modified layers. Also, both external sheets may have a top layer with electrophilically modified fibre, and one or more inward layers without electrophilically modified fibre. Such multiple sheet products can be produced by conventional means, e.g. using a multi headbox as described e.g. in U.S. Pat. No. 5,538,595. The products can be of a tissue type or a non-woven.

The product of the invention can be a layered liquid-absorbing product, such as a sanitary napkin, a diaper or other hygiene product, containing one or more internal layers containing liquid-absorbing material and a modified outer layer. Alternatively, the product of the invention can be a layered product having a modified absorbent core with a non-modified outer layer.

The modified fibre is especially a cellulosic fibre. The cellulosic fibre may be directly obtained from wood pulp, or it may have been pretreated so as to enhance its absorbing capacity or its processability, e.g. in the case of lyocell or viscose fibres. The fibre may also be of a synthetic type such as polyester, polypropylene, polyvinylalcohol, polyamide (nylon), polylactic acid, and the like. Polypropylene and especially polyesters such as polyethylene terephthalate (PET) are preferred for non-wovens. Fibres containing aromatic or other unsaturated groups are particularly preferred, as they are susceptible to oxidation resulting in aldehyde or ketone groups. Different types of synthetic fibres can be used: staple fibres, splittable fibres and continuous filaments.

Where the fibre contains cationic groups, the fibre or fibrous carrier, e.g. paper and paper product, tissue and the like, is positively charged by cationic derivatisation. The cationic derivatisation can be performed by amino- or azido-alkylation, or oxidation to introduce aldehyde functions followed by reaction with amines or other nitrogen-containing reagents. The cationic derivatisation is performed to an extent that allows sufficient coupling of opposite charges, depending on the particular use of the coupling product. In general, a degree of ionisation of 0.1-50 ionic charges per 100 monomer units of the carrier, preferably from 0.5 to 20, most preferably from 1 to 10 charges per 100 units.

Thus, the cationic fibre to be used according to the invention can be a cellulosic material containing at least 0.1 cationic group, preferably at least 1 cationic group, up to e.g. 50 cationic groups per 100 anhydroglucose unit (AGU). In particular the fibre contains between 2 and 20, cationic groups, more in particular between 3 and 10 cationic groups per 100 AGU. The cationic groups may be any charged groups, wherein the charge may be acid-independent, such as in trisubstituted ammonium, trisubstituted phosphonium and disubstituted sulphonium groups, wherein the substituents may be alkyl, alkenyl, aryl and their substituted analogues such as hydroxyalkyl, ammonioalkyl, alkylaryl, arylalkyl, and their cyclic analogues such as in N-pyridylium. Instead, the charge may be acid-dependent such as in amino, and mono- and disubstituted amino groups. An acid-independent charge means that the charge is always present, also under non-acidic conditions (high pH), requiring that the charge-carrying atom (usually nitrogen, sulphur or phosphorus) does not directly carry hydrogen atoms. An acid-dependent charge is only present at sufficiently acidic conditions, i.e. usually when the charge-carrying atom directly binds one or more hydrogen atoms. Acid-independent cationic groups are preferred. Examples of acid-independent charged groups include tri-methylammonio, triethylammonio, N,N-dimethylhydroxyethylammonio, N,N-dimethyl-benzylammonio, 1-methyl-1-piperidino, 1-pyridinio, tributylphosphonio, triphenyl-phosphonio, dimethylsulphonio and the like. Examples of acid-dependent charged groups include amino, ethylamino, dimethylamino, pyrrolidino, morpholino, and the like. The preferred charged group is trimethylammonio $(CH_3)_3N^+$.

The cationic cellulosic fibre can be prepared by first introducing aldehyde groups. A first, convenient method of introducing aldehyde groups consists of oxidation of dihydroxyethylene groups —CHOH—CHOH—, i.e. the 2,3-positions of the cellulosic AGU, using periodate ($MIO_4$ or $M_5IO_6$, wherein M is e.g. hydrogen or an alkali metal or alkaline earth metal or a combination thereof) or similar oxidising agents, resulting in two aldehyde groups. Another useful method involves oxidation of hydroxymethyl groups —$CH_2OH$, i.e. the 6-position of the AGU, using nitric oxides, in particular nitroxyl-mediated ("TEMPO") oxidation using hypochlorite, hydrogen peroxide, peracids such as peroxosulphuric acid, or oxygen as reoxidators, optionally using metal compounds, metal complexes or redox enzymes as cocatalysts. These oxidations have been described in U.S. Pat. No. 3,364,200, NL 9301172, WO 00/50462, WO 00/50463, WO 01/34657 and WO 01/00681, for example. The aldehydes can also be introduced by a combination of oxidation methods, e.g. TEMPO-mediated oxidation followed by periodate oxidation, resulting in aldehydes at positions 2, 3 and 6 of the AGU (see WO 01/34656).

Introduction of carbonyl groups (aldehydes and/or ketones) in both cellulosic and non-cellulosic fibres can be effected by oxidation of unsaturated groups, such as aromatic groups, e.g. phenylene groups in polyesters and polyamides. Suitable oxidation leading to carbonyl functions can be performed with ozone.

The aldehyde-functionalised fibre can conveniently be reacted with an agent having both an unsubstituted amino group ($-NH_2$) for coupling with the aldehyde function, and a cationic group, such as a trialkylammonio group, or a potentially cationic groups such as an amino group, preferably a tertiary amino group (e.g. $N^3,N^3$-dimethyl-1,3-propanediamine). The amino group can be present on an aliphatic (alkyl) position, e.g. as $-CH_2NH_2$, which upon condensation with the aldehyde function ($O=CH-$) results in an imine ($-CH_2N=CH-$), which is then preferably stabilised by reduction to an amine ($-CH_2NH-CH_2-$), e.g. by borohydride reduction, dithionite reduction, or metal-catalysed hydrogenation. Preferably, however, the starting amino group is stabilised, e.g. as a hydrazine ($-NH-NH_2$), a carboxamide ($-CO-NH_2$), a sulphonamide ($-SO_2-NH_2$) or the like, especially a hydrazide ($-CO-NH-NH_2$) or sulphohydrazide ($-SO_2-NH-NH_2$), resulting, upon reaction with the aldehyde, in stable coupling, e.g. as a hydrazone ($-CO-NH-N=CH-$). Very suitable reagents are Girard's reagents T, trimethylammonioacetic hydrazide (($CH_3$)$_3$N$^+$CH$_2$CONHNH$_2$); betaine hydrazide hydrochloride) and P, pyridinioacetic hydrazide. The reaction of Girard's reagents with carbohydrates is known per se, from U.S. Pat. No. 4,001,032.

The reaction with the stabilised amine reagent such as Girard's reagent can be performed by treatment with 1-30 wt. % of reagent with respect to the fibre dry weight to a suspension (0.5-5 wt. %, especially 1-2 wt. %) of the aldehyde-functionalised fibre in water. The pH is usually between 2 and 7, in particular between 4 and 5, the reaction time is typically from 2 minutes to two hours and the temperature is between 20 and 100° C., especially between 36 and 90° C. The fibres are then washed with water to remove excess reagent.

As an alternative, the cationic fibres can be obtained by directly cationising the fibres. Thus, the fibres may be cationised by reaction with a cationising agent, such as 2-chloroethyltrimethylammonium, 3-chloro-2-hydroxypropyltrimethylammonium, or glycidyl trimethylammonium chloride or other epoxide reactants having cationic functions. Further alternatives include binding of cationic polymers, such as poly-ethylenimines and polyamine-amines, to the fibres, optionally using a crosslinker or a binder material, or grafting of cationic monomers, such as diallyldimethylammonium chloride (DADMAC), on to cellulose fibres.

Where the fibre contains functional groups in the form of aldehydes, the aldehyde groups may be introduced by methods known in the art as described above. In case of cellulosic fibres, aldehyde functions may thus be introduced by oxidation. A suitable known example of oxidation of cellulosic material is periodate oxidation (2-3 oxidation) as described above, resulting in a degree of oxidation of choice, e.g. between 0.1 and 30%, wherein a degree of oxidation of 1% means that 1 out of 100 mono-saccharide units has been oxidised to a dialdehyde, i.e. containing 2 aldehyde groups per 100 units. Preferably, the fibre contains 0.5-50 aldehyde (or ketone) groups per 100 units, most preferably 1-20. Another preferred method of introduction of aldehyde groups is 6-oxidation using e.g. TEMPO as described above. Furthermore, carbonyl groups can be introduced by ozone treatment of cellulose fibres. This oxidation method is non-specific and also gives rise to degradation of the cellulose. Cellulose derivatives containing unsaturated groups can be converted to aldehyde-containing derivatives by ozone treatment in a more controlled manner; examples of such an unsaturated substrate include the addition product of allyl glycidyl ether to cellulose as described in WO 01/87986 and the esterification product of unsaturated carboxylic acids with cellulose as described in WO 97/36037. For synthetic fibres, carbonyl groups can be introduced by ozone treatment of polymers containing C—C double bonds or vicinal diols. Carbonyl groups may also be introduced by corona treatment of fibres such as described in EP-A 1158087, or by plasma treatment such as described in WO 00/36216.

Another suitable method of producing aldehyde-modified fibres consists of coupling the fibre with an aldehyde-containing compound, e.g. an aldehyde-containing polymer or oligomer as can be used as a wet-strength agent. Examples of the latter include dialdehyde starch (DAS), cationised dialdehyde starch, and glyoxalated amide polymers such as glyoxalated polyacrylamide (G-PAM). These compounds preferably have a relatively high aldehyde content, e.g. between 5 and 100, especially between 20 and 80 (di)aldehyde groups per recurring unit. These agents can be incorporated in the fibre in relative proportions between e.g. 0.5 and 50% by weight of the fibre, preferably between 2 and 20% by weight.

Modified fibres according to the invention include fibres containing two or more different types of functions capable of interacting with cell wall proteins. For example cellulosic fibres containing both aldehyde groups and cationic groups are also suitable in the products of the invention. For example a polymer fibre may contain 1-20 aldehyde groups and 1-20 cationic groups per 100 monomer units. These mixed functions are accessible e.g. by introduction of aldehyde groups in a manner described above, followed by only partial further reaction of the aldehyde groups to cationic groups.

The fibres thus prepared can be used for making paper, tissues or non-wovens. A tissue paper is defined as a soft absorbent paper having a basis weight below 65 g/m$^2$ and typically between 10 and 50 g/m$^2$. Its density is typically below 0.60 g/cm$^3$, preferably below 0.30 g/cm$^3$ and more preferably between 0.08 and 0.20 g/cm$^3$. Moist tissue paper webs are usually dried against one or more heated rolls. A method, which is commonly used for tissue paper is the so-called Yankee drying, through-air drying (TAD) or impulse drying as described in WO 99/34055. The tissue paper may be creped or non-creped. The creping may take place in wet or dry condition. It may further be foreshortened by any other methods, such as so-called rush transfer between wires.

Apart from cationic or aldehyde-functionalised fibres according to the invention, the tissue paper may comprise pulp fibres from chemical pulp, mechanical pulp, thermo-mechanical pulp, chemo-mechanical pulp and/or chemo-thermo-mechanical pulp (CTMP). The fibres may also be recycled fibres. The tissue paper may also contain other types of fibres enhancing e.g. strength, absorption or softness of the paper. Such fibres may be made from regenerated cellulose or synthetic material such as polyolefin, polyesters, polyamides etc.

The tissue paper may comprise one or more layers. In the case of more than one layer this is accomplished either in a multi-layered headbox, by forming a new layer on top of an already formed layer or by couching together already formed layers, or by depositing dry fibres on a wet formed fibre as described in EP-A 0 332 618. These layers cannot or only with considerable difficulty be separated from each other and are joined mainly by hydrogen bonds. The different layers may be identical or may have different properties regarding for example fibre composition and chemical composition. One or more layers may comprise cationic and/or aldehyde-modified fibres according to the invention.

The tissue paper coming from the tissue machine as a single-ply paper sheet may be converted to the final tissue product in many ways, for example embossed, laminated to a multi-ply product, rolled or folded. A laminated multi-ply tissue product comprises at least two tissue plies, which are often joined either by an adhesive or mechanically. One or more plies may comprise cationic and/or aldehyde-modified fibres according to the invention. In the case of a tissue paper or nonwoven, preferably the outer layers comprise modified fibres as according to the invention. The adhesive may be applied all over the paper or just in regions, for example dots or lines, or only along the edges of the product. The mechanical methods are mainly embossing either over the entire area of the plies or only along the edges, so called edge embossing. In the final product the plies as mostly easy detectable and can often be separated from each other as single plies.

In some more detail, a two layered, two-ply web can be comprised of two plies in juxtaposed relation, each ply having an inner layer and an outer layer. Outer layers may contain short paper making-fibres; whereas inner layers may contain long paper making fibres. In another embodiment, tissue paper products are formed by placing three single-layered tissue paper webs in juxtaposed relation. In this example, each ply is a single-layered tissue sheet made of softwood or hardwood fibres. The outer plies preferably comprise the short hardwood fibres and the inner ply preferably comprises long softwood fibres. The three plies are combined in a manner such that the short hardwood fibres face outwardly. In a variation of this embodiment each of two outer plies can be comprised of two superposed layers. In another embodiment, tissue paper products are formed by combining three layers of tissue webs into a single-ply. In this example, a single-ply tissue paper product comprises a three-layer tissue sheet made of softwood and/or hardwood fibres. The outer layers preferably comprise the short hardwood fibres and the inner layer preferably comprises long softwood fibres. The three layers are formed in a manner such that the short hardwood fibres face outwardly.

The term nonwoven is applied to a wide range of products, which in term of their properties are located between the groups of paper and cardboard on the one hand, and textiles on the other hand. As regards nonwoven a large number of extremely varied production processes are used, such as the air-laid, wetlaid, spunlaced, spunbond, melt-blown techniques etc. Nonwovens represent flexible porous fabrics that are not produced by the classical methods of weaving or knitting, but by intertwining and/or by cohesive and/or adhesive bonding of typical synthetic textile fibres, which may for example be present in the form of endless fibres or fibres prefabricated with an endless length, as synthetic fibres produced in situ or in the form of staple fibres. Alternatively they may be made from natural fibres or from blends of synthetic fibres and natural fibres.

The invention further provides an absorbent article such as a pant-type diaper, which will effectively enable diapers to lie sealingly against and shape conformingly to the wearer's body, even when the pad is full of liquid. Other absorbent articles in which the modified fibre of the invention may be incorporated include incontinence devices, sanitary towels, sanitary napkins and the like The modified fibres according to the invention allow to reach a sufficient degree of bacteria-trapping activity in such absorbent articles and especially the absorption pad while maintaining it biodegradable. A pant diaper according to the invention may include an elongated absorbent pad which is enclosed between an inner liquid-permeable casing layer and an outer liquid-impermeable casing layer. The inner casing layer and/or the outer casing layer may comprise modified fibres according to the invention. It is to be understood that it is well within the scope of the invention to put the modified fibres in distinct layers or mixed with regular cellulosic fibres or polymeric hydrocolloidal material or mixed even with both cellulosic fibres and polymeric hydrocolloidal material. Different combinations with mixed layers and distinct layers are also possible.

The liquid absorbing material in the absorbent article is suitably manufactured by one or more layers of cellulose pulp. The pulp may originally be in the form of rolls, bales or sheets, which at the manufacture of the sanitary towel is dry-defibrated and transmitted in fluffed form to a pulp mat, sometimes including so-called super-absorbents, which are polymers having the ability to absorb water or bodily fluids in an amount of several times their own weight. An alternative to this is to dry-form a pulp mat, such as described in WO94/10956. Examples of other usable absorbent materials are different kinds of natural fibres, such as cotton fibres, peat or the like. Naturally, it is also possible to use absorbent synthetic fibres, or particles of a high-absorbing polymer material of the type, which at absorption chemically bind large amounts of liquid, during the formation of a liquid-containing gel, or mixtures of natural fibres or synthetic fibres. The liquid absorbing material may further comprise additional components, such as form-stabilising means, fluid-spreading means, or binders, such as for example thermoplastic fibres, which have been heat-treated to hold short fibres and particles to a connecting unit. It is also possible to use different types of absorbing foam materials in the absorbent body.

It is possible to add antimicrobial agents to the modified fibres according to the invention, but the use of such additional agents is not absolutely necessary and may even be disadvantageous in some cases.

Where the product containing the modified fibre according to the invention is an absorbent hygiene product, such as a diaper or a sanitary napkin, the further composition and use of the product can be as conventional. Where the product is a wiping tissue, it can be used for cleaning or treating surfaces that are suspected to carry microorganisms, such as kitchen tables, bathroom equipment and other household and industrial surfaces. The cleaning treatment may comprise simple wiping, or it may involve additional treatments, such as wetting, using disinfectants, cleaning agents or the like.

EXAMPLE 1

Preparation and Characterisation of Cationic Lyocell Fibres by Treatment with Glycidyl Trimethyl Ammonium Chloride Sample Preparation Sample A: Lyocell fibres, manufactured by Lenzing with a length of 38 mm and a fibre weight/length unit of 1.3 dtex, were carded. The fibres were then modified as follows: 10 g fibres were mixed with a solution of 6.7 g NaOH in 28.5 ml $H_2O$ in an ice-bath for 30 min. Thereafter, 46.74 g of glycidyl trimethyl ammonium chloride (GTAC; Sigma Aldrich, Sweden) was added with 20 ml $H_2O$ to the fibre suspension, which then was heated to 80-85° C. using a water bath. After 30 min. the fibres were washed with 4% NaCl by repeated decanting. When the washing liquid showed a neutral pH, the fibres were added to 2.5 l of a 4% HCl solution and kept overnight in this medium. Then the fibres were washed with a 2% NaCl solution, and the fibres were washed until a neutral pH was achieved.

Samples B-E: Lyocell fibres were treated as Sample A except that the following amounts of GTAC were used.

|         | absolute | relative to sample A |
|---------|----------|----------------------|
| Sample B: | 23.37 g | 0.50 |
| Sample C: | 16.36 g | 0.35 |
| Sample D: | 9.35 g  | 0.20 |
| Sample E: | 4.67 g  | 0.10 |

Charge Characterisation of Cationic Fibres

For determination of the fibre charge, polyelectrolyte titration was used. 0.5 g fibre was added to 100 ml of a polyacrylate solution. Sodium polyacrylate with a molar weight of 8000 g/mol (Sigma Aldrich, Sweden) was used in these tests. The concentration of the polymer solutions was from 50 mg/l to 375 mg/l and several fibre/polymer blendings were prepared for each charge determination.

The pH was adjusted to 8.5 for each sample. Then the samples were thoroughly mixed by shaking for 10 minutes followed by separation of fibres and liquid achieved by filtration on a Büchner funnel equipped with a Munktell filterpaper (pre weighted) of the grade Munktell no 3. The fibres were dried in an oven at a temperature of 105° C. and weighed in order to determine the amount of analysed fibre. The liquid was titrated with a 0.1 g/l Polybrene® solution and the equivalence point was determined by the aid of a Mütec LPCD (particle charge detector) (1), which measures the zeta potential. The point of equivalence is indicated by a zero zeta-potential. By this procedure the amount of adsorbed polyacrylate/g fibre can be determined as a function of the polyacrylate concentration in the solution and hereby an adsorption isotherm could be achieved. The fibre charge can then easily be determined by extrapolation of the plateau to zero concentration. This value is then multiplied with the charge/weight unit of polyacrylate at the present pH.

The following results were achieved:

| Sample | Fibre charge (μ equivalents/g) |
|--------|-------------------------------|
| A | 770 |
| B | 642 |
| C | 556 |
| D | 257 |
| E | 60  |

Determination of Bacteria-Removing Capability

The ability of the fibres to absorb *Lactobacillus plantarum* was tested by adding the dry fibres to a solution of bacteria and allowing the fibres to absorb bacteria for 10 minutes. The fibres were then removed from the bacteria solution and the reduction of the concentration of the bacteria solution was measured. Unmodified carded lyocell fibres were used as a reference.

In addition to *Lactobacillus*, which are non-pathogenic bacteria, also *Staphylococcus aureus* and *Escherichia coli* were tested. *S. aureus* was chosen as a representative of the gram positive bacteria because it may cause problems both in health care and in food preparation. In addition this is one of the standard bacteria used in testing disinfectants and other cleaners. The bacteria *E. coli* was chosen as a representative of the gram negative bacteria for similar reasons. The day to day variation of the amount adsorbed by the reference fibers is due to natural variation in the bacteria. For comparing the results, a normalised reduction was defined as 'reduction in bacteria obtained by a modified fibre/reduction obtained by the reference fibre measured on the same day'. The results were as follows:

| SAMPLE | Reduction in bacteria (*Lactobacillus plantarum*) | |
|--------|---------------------------|------------|
|        | Concentration (abs units) | Normalised |
| Reference (day 1) | 0.110 ± 0.040 | 1 |
| B | 0.513 ± 0.029 | 4.7 |
| E | 0.097 ± 0.036 | 0.9 |
| Reference (day 2) | 0.052 ± 0.011 | 1 |
| C | 0.220 ± 0.067 | 4.2 |
| D | 0.196 ± 0.064 | 3.8 |

| SAMPLE | Reduction in bacteria (*Staphylococcus aureus*) | |
|--------|---------------------------|------------|
|        | Concentration (abs units) | Normalised |
| Reference (day 3) | 0.024 ± 0.013 | 1 |
| B | 0.196 ± 0.019 | 12.0 |

| SAMPLE | Reduction in bacteria (*Escherichia coli*) | |
|--------|---------------------------|------------|
|        | Concentration (abs units) | Normalised |
| Reference (day 4) | 0.133 ± 0.068 | 1 |
| B | 0.165 ± 0.072 | 1.2 |

EXAMPLE 2

Preparation and Characterisation of Cationic Lyocell Fibres by Periodate Oxidation Followed by Reaction with Girard's Reagent T Sample Preparation Lyocell fibres (40 g), carded as described in example 1, were suspended in 4 liters of a solution of sodium periodate (5.3 g, 25 mmol) with the pH adjusted to 5. The suspension was left in the dark at room temperature for 6 days. Then, the sodium iodate formed during the reaction was removed by washing the fibres with water. Subsequently, the fibres were resuspended in 2 liters of water, Girard's reagent T (trimethylammonioacetic hydrazide) was added (8 g, 50 mmol) and the mixture was stirred for 2 hours at 40° C. Then the fibres were thoroughly washed with water, dewatered as much as possible and dried in a fluidised bed dryer at 40° C.

Determination of Charge

The charge of the fibres was determined according to the method described in Example 1. The charge of the modified fibres was 320 μeq/g.

Determination of Bacterial Removing Capability

The ability of the fibres to adsorb bacteria was measured using the method described in Example 1 with the following results.

| Sample | Reduction in bacteria concentration | |
|--------|-------------|--------------|
|        | (abs units) | (normalised) |
| Reference (day 5) | 0.070 ± 0.018 | 1 |
| Cationic fibre | 0.218 ± 0.017 | 3.1 |

Examples 1 and 2 clearly illustrate that all fibres with charge greater than 60 µeq/g (samples B, D, E, and Lyocell prepared with Girard's reagent) adsorbed significantly more bacteria than the reference (untreated Lyocell). The treated fibres were prepared using two different chemical routes demonstrating that the effect is not specific to a particular type of cationic modification.

EXAMPLE 3

Preparation and Characterisation of Aldehyde Lyocell Fibres by Periodate Oxidation Lyocell fibres, manufactured by Lenzing with the length 38 mm and the fibre weight/length unit 1.3 dtex, were carded. These fibres were oxidised to a degree of 10% as follows: fibres (40 g; 247 mmol) were suspended in 4 liters of a solution of sodium periodate (5.3 g, 25 mmol) with the pH adjusted to 5. The suspension was left in the dark at room temperature for 6 days. Then, the sodium iodate formed during the reaction was removed by washing the fibres 3 times with excess water. Lyocell with higher oxidation degrees (30%, 50%) were prepared in a similar way, except that more sodium periodate was used (15.9 g for 30% and 26.5 g for 50%). The aldehyde content was determined by titration with hydroxylamine. Hydroxylamine hydrochloride (Sigma) (1 g) was dissolved in 40 mL water and heated at 50° C. The pH was adjusted to 3.2. The oxidised lyocell (500 mg) was added. Due to reaction of the aldehydes with hydroxylamine, a pH-drop was observed. From the amount of sodium hydroxide (0.5M) solution needed to keep the pH at 3.2, the aldehyde content could be calculated. The resulting aldehyde contents were as follows:

Aldehyde lyocell 10%: 750 µmol/g aldehyde (=6%)
Aldehyde lyocell 30%: 3500 µmol/g aldehyde (=28.5%)
Aldehyde lyocell 50%: 5110 µmol/g aldehyde (=41.5%)
Determination of Bacterial Removing Capability:

The ability of the fibres to absorb *Lactobacillus plantarum* was tested by adding the dry fibres to a solution of bacteria and allowing the fibres to absorb bacteria for a period of 10 minutes. The fibres were then removed from the bacteria solution and the reduction of the concentration of the bacteria solution was measured. Besides *Lactobacillus*, which is a non-pathogenic bacteria, also *Staphylococcus aureus* and *Escherichia coli* were tested. *Staphylococcus aureus* was chosen as a representative of the gram positive bacteria because it is a bacteria that may cause problems both in health care and in food preparation settings. In addition this bacteria is one of the standard bacteria used in testing disinfectants and other cleaners. The bacteria *Escherichia coli* was chosen as a representative of the gram negative bacteria for similar reasons. The results were as follows:

| SAMPLE | Reduction in bacteria (*Lactobacillus plantarum*) Concentration (abs units) | Normalised |
|---|---|---|
| Lyocell fibre (Day 1) | 0.070 ± 0.018 | 1 |
| Aldehyde lyocell (10%) | 0.255 ± 0.035 | 3.6 |
| Lyocell fibre (Day 2) | 0.067 ± 0.012 | 1 |
| Aldehyde lyocell (10%) | 0.157 ± 0.016 | 2.3 |
| Aldehyde lyocell (30%) | 0.165 ± 0.009 | 2.5 |
| Aldehyde lyocell (50%) | 0.105 ± 0.030 | 1.6 |

| SAMPLE | Reduction in bacteria (*Staphylococcus aureus*) Concentration (abs units) | Normalised |
|---|---|---|
| Lyocell fibre (Day 3) | 0.022 ± 0.018 | 1 |
| Aldehyde lyocell (10%) | 0.196 ± 0.019 | 8.9 |
| Aldehyde lyocell (30%) | 0.164 ± 0.048 | 7.5 |

| SAMPLE | Reduction in bacteria (*Escherichia coli*) Concentration (abs units) | Normalised |
|---|---|---|
| Lyocell fibre (Day 4) | 0.241 ± 0.047 | 1 |
| Aldehyde lyocell (10%) | 0.355 ± 0.047 | 1.47 |
| Aldehyde lyocell (30%) | 0.371 ± 0.056 | 1.54 |

The modified samples all removed significantly more (1.5 up to 8.9 times more) bacteria than the reference.

EXAMPLE 4

Characterisation of Aldehyde-Modified Tork 606 Sheets by Periodate Oxidation Tork 606 is a non-woven material that is produced from 35% polyester (PET, 15 mm, 0.6 dtex), 15% Lyocell (12 mm, 1.4 dtex) and 50% Vigor cellulose pulp. This material was modified with aldehydes by periodate oxidation (oxidation degree 2% and 10%, aldehyde content 240 µeq/g and 540 µeq/g, respectively). The aldehydes are introduced on the cellulose fraction of the sheets. Both oxidation and aldehyde titration were performed as described in Example 3 for the lyocell fibres.

In the wiping test, a steel plate is covered with a mixture of 1 egg yolk and 1 dl of 3% milk and a solution of bacteria (*Staphylococcus aureus*). The plates are dried and then 1 mL of water is placed on the upper edge of the plate. The test paper is wrapped around a paper holder with a specific weight and is placed over the line of water and pulled once vertically and once horizontally across the soiled area without pressing on the holder. The plate is than covered with agar and incubated for 2 days. The colonies of bacteria are then counted. The number of colonies remaining after wiping with a test paper was compared with the number remaining after wiping with unmodified Tork 606. In the case of periodate oxidation, the reference used was unmodified Tork 606 washed with water, since periodate oxidation is performed in aqueous medium.

As can be seen in the table below, the 2% oxidised Tork 606 removed more bacteria than the reference. Periodate oxidised Tork 606 samples became stiffer and less absorbing, especially at higher oxidation degrees (10%), which may explain the lower performance at higher oxidation degree (10%).

| SAMPLE | | Wiping result (number of remaining bacteria after wiping) (median of 5 test samples/ median of 5 references) |
|---|---|---|
| Tork 606 | | 1 |
| Ref: Washed Tork 606 | (Test day 1) | 1.5 |
| Periodate ox. Tork 606 | 2% (Test day 1) | 0.8 |

-continued

| SAMPLE | | Wiping result (number of remaining bacteria after wiping) (median of 5 test samples/ median of 5 references) |
|---|---|---|
| | 10% (Test day 1) | 3.5 |
| Ref: Washed Tork 606 | (Test day 2) | 16.8 |
| Periodate ox. Tork 606 | 2% (Test day 2) | 14.4 |
| | 10% (Test day 2) | 54.5 |

EXAMPLE 5

Preparation and Characterisation of
Aldehyde-Modified Tork 606 Sheets by Ozonation A Tork 606 sheet was placed in a round bottom flask on a rotation evaporator equipment. Ozone gas generated with an ozone generator from oxygen was passed through a 10% acetic acid solution and was then passed in the flask with the Tork 606 sheet. The dose was 6.4 g/hour. After reaction, excess ozone and acetic acid was removed by evaporation in the fume hood. By ozonation, aldehydes (and ketones) are introduced in the cellulose fraction of the sheets as well as in the synthetic fibre (PET). The aldehyde content was determined by titration with hydroxylamine as described in example 3 and was between 100 and 150 µeq/g.

The bacteria removing properties were determined using the wiping method as described in Example 4.

As can be seen in the results table below, 3 out of 5 ozonated Tork 606 removed significantly more bacteria than the reference Tork 606 does. One removed an equal amount of bacteria and one removed less bacteria.

| SAMPLE | | Wiping result (median of 5 test samples/ median of 5 references) |
|---|---|---|
| Tork 606 | | 1 |
| Ozonated Tork 606 | (Test day 1) | 0.1 |
| | (Test day 2) | 8.5 |
| | (Test day 3) | 0.2 |
| | (Test day 4) | 0.5 |
| | (Test day 5) | 1.1 |

The invention claimed is:

1. A process of immobilising micro-organisms in a hygiene product comprising:
   contacting a medium suspected of containing micro-organisms with a hygiene product containing a fibre modified with functions capable of interacting with microbial cell wall biopolymers,
   wherein the fibre comprises a cationic fibre containing 2-20 cationic charges per 100 monomer units of the fibre.

2. The process according to claim 1, wherein the functions capable of interacting with microbial cell wall biopolymers are functions capable of interacting with anionic groups or amine groups.

3. The process according to claim 1, wherein the cationic fibre contains 3-10 cationic charges per 100 monomer units of the fibre.

4. The process according to claim 1, wherein the cationic fibre comprises cationic cellulose obtainable by oxidation of the cellulose to introduce aldehyde groups, followed by reaction of aldehyde groups with a nitrogen-containing reagent carrying a cationic group.

5. The process according to claim 1, wherein the cationic fibre comprises cationic cellulose obtainable by reacting the fibre with a nitrogen-containing reagent carrying a cationic group.

6. The process according to claim 1, wherein the modified fibre further comprises a fibre containing aldehyde groups.

7. The process according to claim 6, wherein the aldehyde-containing fibre contains 0.5-50 aldehyde groups per 100 monomer units of the fibre.

8. The process according to claim 6, wherein the aldehyde-containing fibre is obtainable by oxidation of the fibre.

9. The process according to claim 6, wherein the aldehyde-containing fibre is obtainable by coupling an aldehyde-containing polymer to the fibre.

10. The process according to claim 6, wherein the fibre comprises cellulose.

11. The process according to claim 1, wherein the fibre comprises polyethylene terephthalate.

12. The process according to claim 1, wherein the product includes at least one layer that contains the modified fibre and at least one layer that does not contain the modified fibre.

13. The process according to claim 12, wherein the product includes a surface layer that contains the modified fibre.

14. The process according to claim 1, wherein the product is a homogeneous product containing the modified fibre and non-modified fibre.

15. The process according to claim 1, wherein the product is a sanitary napkin or a diaper.

16. The process according to claim 1, wherein the fibre is a cellulosic fibre containing 0.1 to 50 cationic groups per anhydroglucose unit.

17. The process according to claim 16, wherein the cationic groups includes trisubstituted ammonium, trisubstituted phosphonium or disubstituted sulphonium groups.

18. The process according to claim 1, wherein the fibre has been directly cationised by reacting with a cationising agent selected from the group consisting of 2 chloroethyl-trimethylammonium, 3-chloro-2-hydroxypropyltrimethyl-ammonium, and glycidyl trimethyl-ammonium chloride.

19. The process according to claim 1, wherein the fibre is a cellulosic fibre that has been treated with glycidyl trimethyl ammonium chloride.

20. The process according to claim 1, wherein the fibre is a cellulosic fibre that has been treated with trimethyl-ammonio-acetic hydrazide.

* * * * *